United States Patent
Webber et al.

(10) Patent No.: US 11,762,220 B2
(45) Date of Patent: Sep. 19, 2023

(54) MULTIFOCAL OPHTHALMIC LENSES AND RELATED METHODS

(71) Applicant: CooperVision International Limited, Fareham (GB)

(72) Inventors: Martin Webber, Southampton (GB); Percy Lazon de la Jara, San Ramon, CA (US)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 189 days.

(21) Appl. No.: 17/228,757

(22) Filed: Apr. 13, 2021

(65) Prior Publication Data

US 2021/0341757 A1 Nov. 4, 2021

Related U.S. Application Data

(60) Provisional application No. 63/017,975, filed on Apr. 30, 2020.

(51) Int. Cl.
*G02C 7/06* (2006.01)

(52) U.S. Cl.
CPC ..................... *G02C 7/06* (2013.01)

(58) Field of Classification Search
CPC ........................................ G02C 7/06
USPC ............. 351/159.41, 159.52, 159.66, 159.68
See application file for complete search history.

(56) References Cited

U.S. PATENT DOCUMENTS

| | | |
|---|---|---|
| 7,766,478 B2 | 8/2010 | Phillips |
| 7,832,859 B2 | 11/2010 | Phillips |
| 8,240,847 B2 | 8/2012 | Holden et al. |
| 8,950,860 B2 | 2/2015 | Tse et al. |
| 9,594,259 B2 | 3/2017 | Brennan et al. |
| 9,829,722 B2 | 11/2017 | Tse et al. |
| RE47,006 E | 8/2018 | To et al. |
| 10,061,143 B2 | 8/2018 | Brennan et al. |
| 10,268,050 B2 | 4/2019 | To et al. |
| 10,416,476 B2 | 9/2019 | Lin et al. |
| 10,429,670 B2 | 10/2019 | Newman |

(Continued)

FOREIGN PATENT DOCUMENTS

| | | |
|---|---|---|
| EP | 0622653 A1 | 11/1994 |
| EP | 2761359 A1 | 8/2014 |

(Continued)

OTHER PUBLICATIONS

Search Report issued in corresponding United Kingdom Patent Application No. GB2106178.3 dated Oct. 6, 2021 (3 pages).

(Continued)

*Primary Examiner* — James R Greece
*Assistant Examiner* — Sharrief I Broome
(74) *Attorney, Agent, or Firm* — Kilyk & Bowersox, P.L.L.C.

(57) ABSTRACT

A multifocal ophthalmic lens wherein a first surface of the lens is shaped to form a surface power map and a second surface of the lens is shaped to form a second surface power map. The first surface power map and the second surface power map together form a lens power map. The first surface power map, the second surface power map, or the lens power map comprises a spiral. The spiral has a variation across at least a portion of the lens. Methods of making and using such lenses are also provided.

18 Claims, 6 Drawing Sheets

(56) References Cited

U.S. PATENT DOCUMENTS

| | | | |
|---|---|---|---|
| 2003/0117577 A1 | 6/2003 | Jones et al. | |
| 2005/0057720 A1* | 3/2005 | Morris | G02C 7/042 351/159.44 |
| 2007/0091260 A1* | 4/2007 | Guillon | G02C 7/081 351/159.05 |
| 2011/0234974 A1* | 9/2011 | Lawu | G02C 7/06 623/6.11 |
| 2012/0062836 A1* | 3/2012 | Tse | G02C 7/042 351/159.41 |
| 2014/0211313 A1* | 7/2014 | Dobschal | A61F 2/1618 359/569 |
| 2014/0293426 A1* | 10/2014 | Dobschal | G02B 3/10 703/2 |
| 2016/0313572 A1* | 10/2016 | Haddock | G02C 7/083 |
| 2016/0377884 A1 | 12/2016 | Lau et al. | |
| 2017/0115509 A1 | 4/2017 | Brennan et al. | |
| 2018/0275427 A1 | 9/2018 | Lau et al. | |
| 2019/0171036 A1* | 6/2019 | Weeber | G02C 7/06 |
| 2019/0212580 A1 | 7/2019 | To et al. | |
| 2019/0369416 A1* | 12/2019 | Sankaridurg | G02C 7/06 |
| 2022/0050355 A1* | 2/2022 | Geday | G02B 3/08 |

FOREIGN PATENT DOCUMENTS

| | | |
|---|---|---|
| WO | 02061497 A1 | 8/2002 |
| WO | 2009012789 A1 | 1/2009 |
| WO | 2012156081 A1 | 11/2012 |
| WO | 2013001299 A1 | 1/2013 |
| WO | 2015004881 A1 | 1/2015 |
| WO | 2020260679 A1 | 12/2020 |

OTHER PUBLICATIONS

International Search Report and Written Opinion issued in corresponding International Patent Application No. PCT/GB2021/051040 dated Aug. 2, 2021 (14 pages).

U.S. Appl. No. 17/228,752, filed Apr. 13, 2021 (39 pages).

U.S. Appl. No. 17/228,755, filed Apr. 13, 2021 (42 pages).

* cited by examiner

MULTIFOCAL OPHTHALMIC LENSES AND RELATED METHODS

This application claims the benefit under 35 U.S.C. § 119(e) of prior U.S. Provisional Patent Application No. 63/017,975, filed Apr. 30, 2020, which is incorporated in its entirety by reference herein.

TECHNICAL FIELD

The present invention concerns multifocal ophthalmic lenses and related methods. More particularly, but not exclusively, this invention concerns a multifocal ophthalmic lens, with a lens power map comprising a spiral, wherein the spiral has a variation across a portion of the lens. The invention also concerns methods of making and using such lenses.

BACKGROUND

In the context of the present disclosure, a multifocal ophthalmic lens is an ophthalmic lens which simultaneously provides focussing to more than one distance. This is typically achieved by subdividing the ophthalmic lens into a plurality of regions. Regions in a first subset of the plurality of regions are provided with a first lens power, corresponding to a first focussing distance (for example distance vision). Regions in a second subset of the plurality of regions are provided with a second lens power, corresponding to a second focussing distance (for example near vision).

In multifocal contact lenses, the plurality of regions are typically formed as concentric circles centred on the optical axis of the contact lens, with the concentric circles alternating between the first lens power and the second. Thus, the power map of an optic zone of a typical multifocal contact lens comprises at least two alternating concentric circles of a first and second lens power. However, such contact lenses can cause difficulties for wearers in changeable light conditions. In lower light conditions, the pupil of the wearer's eye dilates in order to provide a larger aperture for incident light, increasing the amount of light received into the eye and thereby providing improved low-light vision. As conditions brighten, the pupil constricts to provide a smaller aperture and thereby limit the amount of light received into the eye. As the wearer's pupil dilates and constricts, the number of the concentric rings on the contact lens which are positioned across the wearer's entrance pupil will also vary. As the pupil dilates, a greater number of the concentric rings will be positioned across the wearer's entrance pupil. Likewise, as the pupil constricts, fewer of the concentric rings will be positioned across the wearer's entrance pupil. Because the concentric rings alternate between the first lens power and the second lens power, the ratio of the first lens power to the second lens power positioned across the wearer's entrance pupil will vary as the wearer's pupil constricts and dilates. As the pupil constricts, the quantity of only one of near and distance focussing is reduced until the pupil has constricted to the diameter of the next smallest concentric circle. At this point, the quantity of only the other of the near and distance focussing is reduced until the pupil has constricted to the diameter of the next smallest concentric circle again. This cycle repeats as the pupil constricts, causing variation in the ratio of the near focussing to the distance focussing as the pupil constricts. It will be appreciated that the same effect occurs in reverse as the pupil dilates. These variations in the ratio of near to distance focussing can cause distraction to the wearer and even a loss of multifocal vision. Generally, the more constricted the wearer's pupil, the more exacerbated this variation in the ratio. Therefore, in bright conditions in particular when the pupil constricts to near to its minimum size, wearers of such multifocal contact lenses may find that the ability of the multifocal contact lens to provide high acuity in both near and distance vision is impaired. This effect is exacerbated further for two-zone multifocal contact lenses, which are one of the more prevalent designs of multifocal contact lens. Two-zone multifocal contact lenses comprise an inner circle of a first lens power and a single surrounding peripheral ring of a second lens power. Thus, the more the pupil of a wearer of such a contact lens constricts, the less of the second lens power is positioned across the wearer's entrance pupil. In some cases, the pupil may even constrict to the extent that none of the second lens power is positioned across the wearer's entrance pupil, causing a complete loss of multifocal vision. Other multifocal contact lenses may utilize a similar principle but instead of alternating concentric rings may include an aspheric power profile to provide a more gradual transition from near viewing powers to distance viewing powers compared to alternate ring embodiments.

The present invention seeks to mitigate the above-mentioned problems. Alternatively or additionally, the present invention seeks to provide an improved multifocal ophthalmic lens.

SUMMARY

The present invention provides, according to a first aspect, a multifocal ophthalmic lens. A first surface of the ophthalmic lens is shaped to form a first surface power map. A second surface of the ophthalmic lens is shaped to form a second surface power map. The first and second surface power maps together form a lens power map. The first surface power map, the second surface power map, and/or the lens power map comprises a spiral. The spiral has a variation across at least a portion of the lens.

A contact lens having a power map comprising a spiral can provide a more stable ratio of near vision focussing to distance vision focussing in the presence of changes in the pupil size of the wearer. As light conditions change, the wearer's pupil will dilate and constrict in order to regulate the amount of light received into the eye. As conditions brighten, the pupil constricts to reduce the amount of light allowed into the eye. As conditions darken, the pupil dilates to allow more light into the eye. Multifocal contact lenses of the prior art may use alternating concentric rings of near and distance focussing, for example a central circle of distance focussing surrounded by a peripheral circle of near focussing. Alternatively, existing multifocal contact lenses may use aspheric power profiles within the optic zone. As discussed above, these contact lenses suffer from variation in the ratio of near focussing to distance focussing provided across the wearer's entrance pupil as the wearer's pupil dilates and constricts. These variations can cause distraction to the wearer and even a loss of multifocal vision.

A spiral power map as disclosed herein can provide a constant ratio of near focussing to distance focussing across the full range of diameters including the spiral map. Thus, a contact lens having a spiral power map can maintain either a substantially constant ratio (where the spiral covers the whole of the optic zone of the lens) or a monotonically varying ratio (where the spiral covers only a radial subportion of the optic zone of the lens) of near to distance focussing as the pupil constricts or dilates. Thus, a contact lens having a spiral power map provides improved multifocal vision in the presence of variable lighting conditions.

It will be appreciated by the skilled person that, where the power map varies smoothly (for example, as a sinusoid), the power map will comprise lens powers other than simply a first lens power corresponding to near vision and a second lens power corresponding to distance vision. In such a case, the power map will also comprise regions having lens powers between the first and second powers (e.g., intermediate lens powers). It will be appreciated that this does not affect or diminish the advantage described above of providing a consistent and stable variation in the add power positioned across the wearer's entrance pupil. It will be appreciated by the skilled person that this advantage is derived from the fact that, for a spiral power map, the composition of add powers at a particular radius does not vary according to a radial distance from the optical axis of the lens.

According to a second aspect of the invention there is also provided a method of manufacturing a multifocal ophthalmic lens. The method comprises operating a lathe to shape a first surface of one of: a lens, a mould for a lens, or an insert for manufacturing a mould for a lens to form a first surface power map. The method further comprises operating a lathe to shape a second surface of the lens mould or insert to form a second surface power map. The first surface power map and the second surface power map together form a lens power map. The first surface power map, the second surface power map, or the lens power map forms a spiral, the spiral having a variation across at least a portion of the lens. That portion includes the optic zone of the lens.

In a third aspect of the invention there is also provided a method of using the multifocal ophthalmic lens described herein. The methods may be effective in improving the vision of a presbyopic lens wearer (e.g., a person 40 years old or older). Alternatively, the methods may be effective in reducing progression of a refractive error, such as reducing the progression of myopia or hyperopia. When the present lenses are used to reduce the progression of myopia, the methods include a step of providing the ophthalmic lenses to a person whose eyes are able to accommodate. Embodiments of the methods may include a step of providing the ophthalmic lenses to a person that is from about 5 years old to about 25 years old. The providing can be performed by an eye care practitioner, such as an optician or optometrist. Alternately, the providing can be performed by a lens distributor that arranges for the delivery of the ophthalmic lenses to the lens wearer.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which.

DETAILED DESCRIPTION

Figure 1:
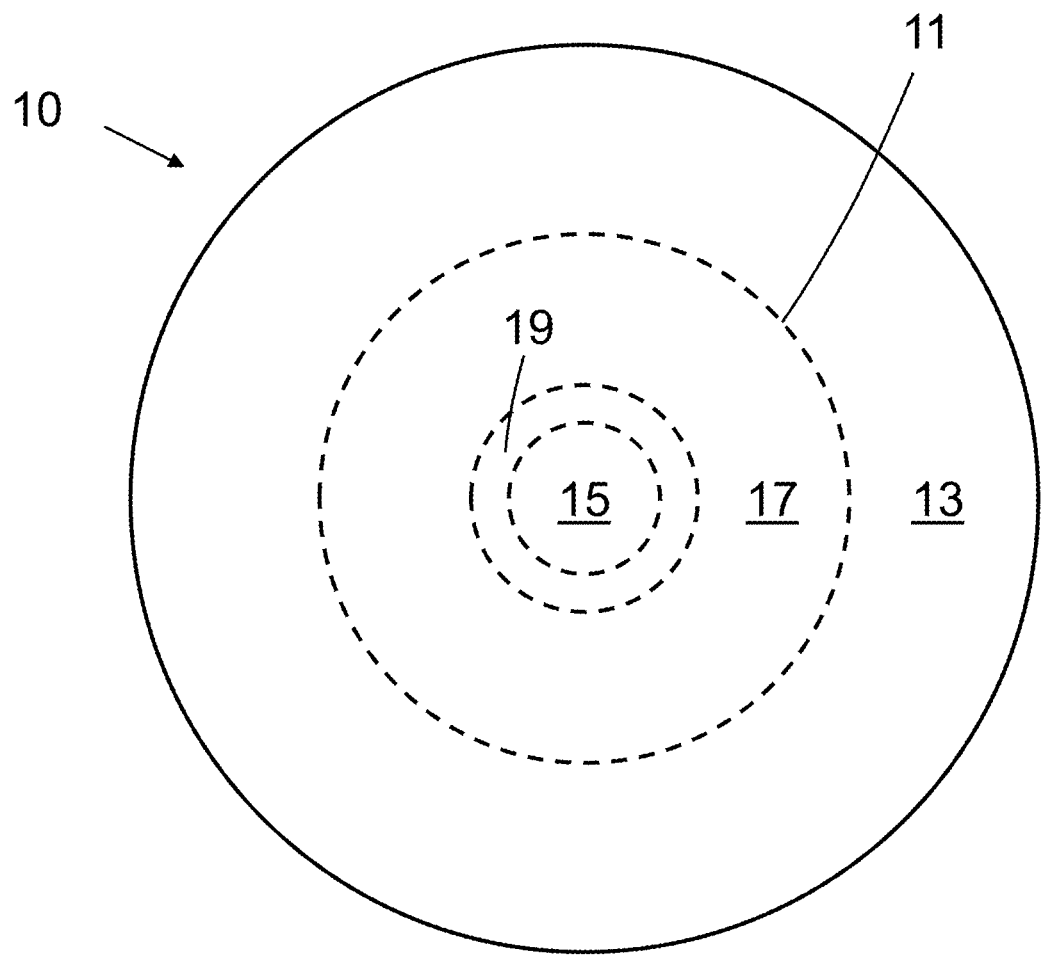
FIG. 1 shows a contact lens according to example embodiments of the invention.

The present invention provides, according to the first aspect, a multifocal ophthalmic lens. A first surface of the lens is shaped to form a first surface power map. A second surface of the lens is shaped to form a second surface power map. It will be appreciated by the skilled person that the variation of a surface comprises a variation in the curvature of the surface. The first and second surface power maps together form a lens power map. The first surface power map, the second surface power map, and/or the lens power map comprises a spiral, the spiral having a variation across at least a portion of the lens.

It will be appreciated that either of the first surface power map and the second surface power map may have a substantially constant power of +0 D across the power map. For the purposes of this description, the respective surface of the lens is still considered to form a surface power map, even though that surface power map ultimately provides no focussing or vision modification.

It may be that the ophthalmic lens is a contact lens. Alternatively, the ophthalmic lens may be an intraocular lens or a spectacle lens.

It may be that the first surface varies across an optic zone of the lens to form the first surface power map. Similarly, it may be that the second surface varies across the optic zone of the lens to form the second surface power map. Thus, it may be that the portion of the lens corresponds to an optic zone of the lens.

It will be appreciated that the lens will comprise an optic zone, which provides vision correction. Contact lenses and intraocular lenses according to embodiments of the invention may also comprise a surrounding peripheral zone, which provides no additional focussing or vision correction. In such embodiments, the peripheral zone may serve merely to help maintain the contact lens in position on or in the wearer's eye. Thus, it will be appreciated by the skilled person that the surface power map is defined by the profile of the first surface across the optic zone of the lens. The profile of the lens surface outside of the optic zone (for example, in a peripheral zone) is not, in the context of the present invention, to be treated as defining the surface power map. Similar considerations also apply to intraocular lenses, which may also comprise an optic zone and (optionally) a peripheral zone.

It may be that the optic zone of a contact lens according to embodiments of the present invention has a diameter of between 4 mm and 9 mm, depending on the type of contact lens. For example, the diameter of the optic zone may be about 5 mm, or about 6 mm, or about 7 mm, or about 8 mm. The diameter of the optic zone of the contact lens may be between 7 mm and 9 mm. The optic zone includes an optical axis that corresponds to the geometric centre of the optic zone.

In the case of spectacle lenses, the entire lens may serve to provide vision correction, rather than just a portion of the lens. Thus, the ophthalmic lens may be a spectacle lens. It may be that the first surface is shaped across the whole of the lens to form the first surface power map.

It may be that the spiral has a first periodic component, in a radial direction extending outwards from the centre of the portion, and a second periodic component, in an azimuthal direction about the centre of the portion. It may be that the first and second components are each formed on a same one of the first and second surface.

The azimuthal direction is to be understood to refer to rotation about the centre of the portion. Thus, a movement in the azimuthal direction equates to a change in angular position about the centre of the portion. It will be appreciated that, in such embodiments, the variation of the power map which forms a spiral is the sum of the first and second periodic components.

It may be that one or both of the first and second periodic components are of constant magnitude across the portion.

It may be that the first periodic component (in the radial direction) has a period of greater than 100 microns. It may be that the second periodic component has a period of greater than 6 degrees. It may be that the period of the first periodic component is greater than 200 microns, preferably greater than 400 microns, and more preferably greater than 800 microns. The period of the first periodic component may be less than 2 mm, preferably less than 1.5 mm, more preferably less than 1 mm. It may be that a period of the second periodic component (in the azimuthal direction) is greater than 6 degrees, preferably is greater than 9 degrees, preferably greater than 18 degrees, and more preferably greater than 36 degrees. The period of the second periodic component may be less than 180, preferably less than 90, more preferably less than 45 degrees.

Thus, in embodiments, it may be that the first periodic component has a period of greater than 100 microns and the second periodic component has a period of greater than 6 degrees, preferably greater than 9 degrees, more preferably greater than 18 degrees, and yet more preferably greater than 36 degrees. In other embodiments, it may be that the first periodic component has a period of greater than 200 microns and the second periodic component has a period of greater than 6 degrees, preferably greater than 9 degrees, more preferably greater than 18 degrees, and yet more preferably greater than 36 degrees. In other embodiments, it may be that the first periodic component has a period of greater than 400 microns and the second periodic component has a period of greater than 6 degrees, preferably greater than 9 degrees, more preferably greater than 18 degrees, and yet more preferably greater than 36 degrees. In other embodiments, it may be that the first periodic component has a period of greater than 800 microns and the second periodic component has a period of greater than 6 degrees, preferably greater than 9 degrees, more preferably greater than 18 degrees, and yet more preferably greater than 36 degrees.

It may be that the variation of the spiral comprises an offset in power. The offset may change according to a radial distance from the centre of the portion. In embodiments, the offset may comprise one of the plurality of components. Thus, the plurality of components may further comprise an offset component which varies (for example, linearly, exponentially, or monotonically) with a radial distance from the centre of the lens. For example, it may be that the offset provides an add power which decays, for example linearly, radially outwards from the centre of the portion.

It may be that a peak power of one or more arms of the spiral varies according to one or both of: a radial distance from the centre of the portion and an azimuthal position about the centre of the portion. It may be that a magnitude of the periodic components changes according to one or both of: a radial distance from the centre of the portion and an azimuthal position about the centre of the portion.

It may be that a peak power of each arm of the spiral does not vary with radial distance from the centre of the portion. It may be that the peak power of at least one arm of the spiral differs from that of the other arms. Thus, it may be said that each arm of the spiral provides a different lens power. It may therefore be that multifocal vision is provided by the arms of the spiral. It may be that the peak power of each arm of the spiral differs from that of the other arms. It will be appreciated that such a feature may be characterised as a variation of the periodic components with respect to both radial distance from the centre of the portion and azimuthal position about the centre of the portion. Thus, it may be that the periodic components vary with respect to both radial distance from the centre of the portion and azimuthal position about the centre of the portion such that the peak power of at least one arm (for example, each arm) of the spiral differs from that of the other arms.

It may be that the power of the first surface power map varies smoothly across the portion. It may be that the power of the second surface power map varies smoothly across the portion. Thus, it may be that the periodic components vary smoothly (for example, as a sinusoid or a rounded square wave). It may be that surface power maps each varies continuously, without any discontinuities. It may be that the power varies across the portion at a rate of less than 80 D/mm, preferably less than 40 D/mm, more preferably less than 20 D/mm. It may be that the surface varies smoothly across the portion. It may be that surface varies continuously, without any discontinuities. Varying the power smoothly can result in a lens surface profile which is easier to manufacture using a lathe. It will be appreciated by the skilled person that manufacturing an ophthalmic lens using a lathe may comprise using a lathe to shape a surface of one or more of a lens (for example a contact lens), a mould for a lens (for example a mould for a contact lens), and an insert for a lens mould (for example an insert for a contact lens mould). Sharp transitions and features can be difficult to achieve using a lathe. Therefore, lenses having such features are often not reproducible with the intended or required definition when manufactured using a lathe. Thus, it will also be appreciated that the term smoothly in this context means smooth enough to enable the desired shaping of the surface of a lens, a mould for a lens, or an insert for a lens mould using a lathe.

The power may vary as a square wave in one or both of the radial and azimuthal directions. The power may vary as a rounded square wave in one or both of the radial and azimuthal directions. The power may vary as a sinusoid in one or both of the radial and azimuthal directions.

The first and second periodic components may vary as one of: a square wave, a sinusoid, and a rounded square wave. The period of one or both of the first and second periodic components may be substantially constant across the portion of the lens. Embodiments of the invention in which the first and second periodic components have a substantially constant period across the portion yield a lens surface profile which is easier to manufacture using a lathe compared to embodiments in which the radial and angular variations are not constant. In the case of contact lenses according to embodiments of the invention, one or both of the first and second periodic components may have a substantially constant period from the optic zone perimeter in towards the optic axis of the optic zone.

It may be that the power variation in each of the radial and angular directions is associated with a respective waveform. In addition, the power distributions of the waveforms may be symmetrical with a substantially equal balance between near vision correction and distance vision correction. Alternately, the power distribution may be biased towards either distance vision correction or near vision correction. Thus, the power distributions of the waveforms may be asymmetric in one or both of the radial direction and the angular direction.

The period of one or both of the first and second periodic components may change according to either or both of a radial distance from the centre of the portion of the lens and an azimuthal position about the centre of the portion. Embodiments of the invention in which the period of one or both of the first and second periodic components change according to position on the lens can provide a lens in which the characteristics of the spiral (for example its rate of rotation or arm width) differ in different regions of the lens.

Changes in the period of the first periodic component (that is the periodic component in the radial direction) may be separated by a blending region, for example of smoothly (for example, linearly) varying period. The blending region may therefore comprise a concentric ring of smoothly (for example, linearly) varying period between a first region having a first period of radial variation and a second region having a second period of radial variation. Alternatively, the blending region may comprise a region of smoothly (for example, linearly) varying lens power. Thus, the blending region may provide a smooth transition between regions of different period radial variation. It may be that regions of different period radial variation are separated by two blending regions and an intervening region of substantially constant lens power. The blending region may have a width (in plan view) from about 25 micrometers to about 200 micrometers.

The spiral may comprise more than two arms, preferably more than 4 arms, more preferably more than 8 arms, yet more preferably more than 16 arms. It will be appreciated by a person skilled in the art that the period of the second periodic component will determine the number of arms on the spiral.

The period of the first periodic component may be between 24 mm and 2 mm. The period of the first periodic component may be between 16 mm and 4 mm. It may be that each arm of the spiral twists through between a quarter of a rotation and 40 rotations. It will be appreciated by a person skilled in the art that the number of rotations that an arm of the spiral twists through is determined by the period of the first periodic component and a radius (or size) of the portion of the lens. It will be appreciated that references to the radius of the portion (for example, an optic zone of a contact lens) refer to a distance of half of a plan view diameter of the portion. In this context, a plan view is intended to be taken as a view along the optical axis of the lens.

It may be that a ratio of the period of the first periodic component to that of the second periodic component is greater than 0.1 mm: 6°. It may be that each arm of the spiral is wider than 0.1 mm, preferably wider than 0.5 mm, more preferably wider than 1 mm. It may be that each arm is between 0.1 mm and 3 mm wide. It may be that each arm is between 0.25 mm and 2 mm wide. It may be that each arm is between 0.5 mm and 1 mm wide. The width of the spiral arms are determined when viewing the power map in plan view (i.e. along the optical axis of the lens), as shown in the accompanying drawings. It will be understood by a person skilled in the art that a width of an arm at a given radius is defined as its perpendicular width (i.e. its width in the direction perpendicular to the given radius). The width of the arm is, in this context, defined as the distance between two points immediately adjacent each side of the arm, both points having either a maximum or a minimum gradient, between which the power undergoes a single positive or negative excursion. The skilled person will appreciate that such a definition of width provides a straight-line measurement of arm width along a tangent to a circle of the given radius. The skilled person will further appreciate that a measurement of width under this definition will differ from a measurement of the width of an arm taken as an arc of a circle having the given radius. Unlike a width measurement under the straight-line width definition, such an arc-based measurement would be proportional to the period of the second periodic component. The magnitude of the difference between the widths obtained by these two methods will depend on the period of the second periodic component in the particular case at hand.

It may be that each arm of the spiral extends from the centre of the portion of the lens to the periphery of the portion. Contact lenses according to embodiments of the invention in which the arms of the spiral extend from the centre of the portion to the periphery of the portion can provide a substantially constant ratio of the first lens power to the second lens power in the presence of varying pupil dilation. Such embodiments thereby provide high acuity multifocal vision in a wide range of light conditions.

It may be that a twist rate of the spiral varies according to a radial distance from the centre of the portion. The twist rate of the spiral will be understood to mean the rate at which the arms of the spiral rotate about the centre of the spiral (i.e. the number of rotations of the arms about the centre of the spiral across a given radial distance). It will be appreciated that a change in the twist rate of the spiral may be the result of a non-proportional change in the period of the first periodic component compared to a change in the period of the second periodic component (for example, by changing the period of the first periodic component whilst maintaining the period of the second periodic component unchanged). It may be that a width of one or more arms of the spiral differs from a corresponding width of the other arms of the spiral. It will be appreciated that such a feature may be defined as the periodic components providing the periodic components with a varying duty cycle across the portion.

It will be appreciated that the lens will have a means lens power. Furthermore, it will be appreciated that the lens will be divided between a first area of the lens having a lens power greater than the mean and a second area of the lens having a lens power less than the mean. It may be that a ratio of the first area to the second area is between 10:1 and 1:10. It may be that a ratio of the first area to the second area is between 5:1 and 1:5. It may be that a ratio of the first area to the second area is between 3:1 and 1:3. It may be that a ratio of the first area to the second area is between 2:1 and 1:2. It may be that a ratio of the first area to the second area is approximately 1:1.

The portion of the lens, which may be an optic zone, may comprise a central region and an outer region. The central region may immediately surround the optical axis of the lens. The central region may be offset from the geometric centre of the lens. For example, it may be desirable to offset the central region from the geometric centre of the lens to allow the optical axis of the offset central region to align with the pupil of the lens wearer due to natural decentration of the lens on the eye. The outer region may surround (for example, immediately surround) the central region. It may be that the power of the central region does not vary periodically across the central region (for example, having substantially constant lens power across the central region). The lens power map in the outer region may comprise the spiral. Thus, it may be said that the outer region comprises the spiral. Providing a contact lens having an optic zone with a central region having a lens power corresponding to distance vision and free from periodic power variation can ensure that the wearer maintains high acuity distance vision even in bright conditions. For example, this may be particularly advantageous to the wearer when driving. Alternatively, it may be that the central region comprises the spiral, and the power of the outer region does not vary periodically across the outer region (for example, having substantially constant lens power across the outer region).

A contact lens may include a peripheral zone, which surrounds the optic zone and which provides no additional focussing or vision correction and serves merely to help maintain the contact lens in position on the wearer's eye. When worn on an eye, the contact lens rests on the cornea and the optic zone approximately covers the pupil of the wearer, in the conventional manner. Thus, it will be understood that contact lenses according to the invention may comprise an optic zone and a surrounding peripheral zone. The optic zone provides vision correction. The peripheral zone does not provide any vision correction, but the peripheral zone may provide other functions (such as helping to maintain the contact lens in position on the eye). The surfaces of the lens within the optic zone provide the first and second power maps, and thereby also the lens power map. The optic zone may therefore optionally comprise central, outer, and transition regions as described above. The optic zone may also comprise one or more blending regions as previously described.

The diameter of the central region may be less than 50%, preferably less than 40%, more preferably less than 30%, of that of the portion. Thus, in contact lenses according to embodiments of the invention, the diameter of the central region may be less than 50%, preferably less than 40%, more preferably less than 30%, of that of the optic zone of the contact lens. The central region may be smaller than the minimum pupil size of a wearer of the contact lens. Embodiments of the invention having a central region which is smaller than the minimum pupil size of the wearer can maintain high acuity near and distance vision in the presence of varying light conditions.

The power of the central region may be substantially constant (for example, the power can vary by less than 0.25 dioptres (D) from the nominal power across the central region). The central region may have a lens power corresponding to distance vision. Contact lenses according to embodiments of the invention in which the central region has a substantially constant lens power corresponding to distance vision can provide high acuity distance vision in bright light conditions, when the pupil is at its minimum size. High acuity distance vision is generally more useful to the wearer than high acuity near vision in bright light conditions because such conditions generally correspond to daytime outdoor environments where the wearer typically has greater need for distance vision than for near vision. Alternatively, the central region may have a lens power corresponding to near vision. Furthermore, the central region may have a lens power that is more positive than the near vision correction power required by the lens wearer. For example, the power of the central region may be +0.25 D to +1.25 D more positive than required by an eye for near vision correction.

The lens may comprise a transition region. The transition region may surround the central region. The outer region may surround the transition region. Thus, the transition region may be positioned between the central and outer regions. It may be that the power of the transition region varies to provide a smooth transition between the central and outer regions. Embodiments of the invention providing a smooth transition between the central and outer regions can enable easier manufacture using a lathe of a lens, a mould for such a lens, or an insert for such a lens mould. Thus, it will be appreciated by the skilled person that smooth in this context means that the lens profile must be smooth enough to be produced using a lathe.

It may be that the spiral is formed entirely on the first surface (i.e. the spiral is formed entirely by the first surface power map). Thus, it may be that the second surface power map does not vary periodically across the portion of the lens. Alternatively, the spiral may be formed entirely on the second surface (i.e. the spiral is formed entirely by the second surface power map). Thus, it may be that the first surface power map does not vary periodically across the portion of the lens. Alternatively, the spiral may be formed by the first and second surfaces together (i.e. the spiral is formed by the superposition of the first and second surface power maps). Contact lenses according to embodiments of the invention in which the optic zone comprises a spiral lens power map can provide a substantially constant ratio of the first lens power to the second lens power in the presence of varying pupil size.

It will be appreciated that either of the first surface power map and the second surface power map may have a substantially constant power of +0 D across the power map. For the purposes of this description, a surface of the lens is still considered to form a surface power map, even if that surface power map ultimately provides no focussing or vision modification.

The first surface power map may vary substantially periodically radially outwards from the centre of the portion. The second surface power map may vary substantially periodically radially outwards from the centre of the portion. The lens power map may vary substantially periodically radially outwards from the centre of the portion. A period of the radial variation of the surfaces may be greater than 100 microns, preferably greater than 200 microns, more preferably greater than 400 microns, and yet more preferably greater than 800 microns.

The first surface power map may vary substantially periodically azimuthally about the optical axis of the lens. The second surface power map may vary substantially periodically azimuthally about the optical axis of the lens. The lens power map may vary substantially periodically azimuthally about the optical axis of the lens. A period of the azimuthal variations of the surfaces may be greater than 6 degrees, preferably greater than 9 degrees, more preferably greater than 18 degrees, and yet more preferably greater than 36 degrees.

The periods and phases of the radial and azimuthal variations of the second surface may be the same as those of the first surface. It will be appreciated that the periods of the azimuthal and radial variations of the first surface power map need not necessarily be the same as those of the second surface power map. The first surface power map and/or the second surface power map may comprise a spiral, for example a spiral having a variation across the portion. The second surface power map may comprise a spiral matching a spiral of the first surface power map. In such embodiments, the power map of the lens as a whole also comprises a spiral.

Embodiments of the invention comprising contact lenses with a spiral lens power map can provide a substantially constant ratio of the first lens power to the second lens power in the presence of varying pupil size.

It may be that the spirals provided by the first and second surfaces twist in opposing directions. Thus, the first and second surface power maps can be said to comprise counter-rotating spirals. The spirals provided by the first and second surface power maps may be the same but for the opposing twist directions. Embodiments of the invention in which the first and second surface power maps comprise counter-rotating spirals can give a lens power map which approximates a dartboard-like pattern of alternating annular rings. It will be appreciated by a person skilled in the art that the lens power map is formed by the superposition of the first and second surface power maps. Thus, it will also be appreciated that the pseudo-dartboard pattern is provided by the combination of the first and second surface power maps, each of which retains the previously described benefits of ease of manufacture. Thus, such embodiments can enable easier manufacture of a lens having a pseudo-dartboard power map using a lathe.

The lens power map may comprise a plurality of sections. Sections in the plurality of sections may provide a first power corresponding to distance vision or a second power corresponding to near vision. The sections may be arranged on the lens such that they alternate radially and/or azimuthally between the first power and the second power. Accordingly, the first power may be between 0 dioptres (D) and −10 D. The first power may be from −0.25 D to −6.00 D. The second power provided in the present lenses may be more positive than the first power of the lens, for example, the second power may be from 1 D to 5 D more positive than the first power. The second power may be 1 D to 4 D more positive than the first power. The second power may be 2 D to 3 D more positive than the first power. The second power may vary, such as may occur when providing discrete sections of defocus with more positive power than the first power, such that some of the section may have a second power of +1 D, some sections may have a second power of +2 D, and some sections may have a second power of +3 D. The variation of the second power may occur within the same arm, or the variation of the second power may occur in different arms.

It may be that, at a pre-determined radial distance from the centre of the portion, the spiral changes its direction of rotation. Thus, it may be that a first section of the lens comprises a clockwise rotating spiral and a second section of the lens comprises an anti-clockwise rotating spiral. Such sections may be formed as concentric rings, for example centred on the centre of the portion. Sections of the lens having different directions of rotation may be separated by an intervening section of substantially constant lens power. It may be that the lens comprises more than one change in the direction of rotation of the spiral (for example, with each change in direction having an intervening section of substantially constant lens power).

The multifocal lens may be a myopia control lens, and the multifocal lens may be configured to reduce the progression of myopia in a person whose eyes are able to accommodate. The multifocal lens may be suitable for providing vision correction, and the multifocal lens may be configured to provide distance vision correction and near vision correction to a person whose eyes are unable to accommodate sufficiently (e.g., a person 40 years old or greater).

A contact lens according to the invention may comprise a ballast to orient the lens when positioned on the eye of a wearer. Such a ballast may be provided by a peripheral zone of the contact lens. It may be that the contact lens provides particular benefit to the wearer in a given orientation. Embodiments of the invention incorporating a ballast into the contact lens will, when placed on the eye of a wearer, rotate under the action of the wearer's eyelid to a pre-determined angle of repose; for example the ballast may be a wedge and the rotation may result from the action of the eyelid on the wedge. By positioning the ballast in the contact lens, it is possible to ensure that the angle of repose corresponds to a lens orientation providing particular benefit to the wearer.

The present invention provides, according to the second aspect, a method of manufacturing a multifocal ophthalmic lens (for example a contact lens). The method comprises operating a lathe to shape a first surface of one of: a lens (for example a contact lens), a mould for a lens (for example a mould for a contact lens), or an insert for manufacturing a mould for a lens (for example an insert for a mould for a contact lens). The first surface is shaped to form a first surface power map. The method further comprises operating a lathe to shape a second surface of the lens, mould or insert. The second surface is shaped to form a second surface power map. The first and second surface power maps together form a lens power map. The first surface power map, the second surface power map, and/or the lens power map comprises a spiral, the spiral having a variation across at least a portion of the lens, mould or insert.

The first surface may be shaped such that the surface power map varies substantially periodically both radially outwards from and azimuthally about the centre of the portion. It may be that a period of the radial variation is greater than 100 microns. It may be that a period of the azimuthal variation is greater than 6 degrees.

It may be that the method comprises operating a lathe to shape the surface of at least a portion of a lens. Alternatively or additionally, the method may comprise operating a lathe to shape the surface of at least a portion of a mould for a lens. Alternatively or additionally, the method may comprise operating a lathe to shape the surface of at least a portion of an insert for manufacturing of a mould for a lens. It will be appreciated by the skilled person that the further removed the subject of the shaping by the lathe is from the lens, the less feature definition that will reproduced on the resulting lens. Thus, for example, shaping the surface of a lens using a lathe enables more defined surface features than will be achievable when using the lathe to shape the surface of a mould for a lens.

The method further comprises operating a lathe to shape a second surface of the portion of the lens, the mould, or the insert. The second surface may be shaped to vary across at least the portion to form a second surface power map comprising a spiral. The second surface may be shaped such that the second surface power map varies substantially periodically both radially outwards from and azimuthally about the centre of the portion. A period of the radial variation may be greater than 100 microns. A period of the azimuthal variation may be greater than 6 degrees. The second surface may be shaped such that the second surface power map varies as a mirror image of the first surface. The second surface may be shaped such that the spiral formed by the first surface power map twists in the opposite direction to that formed by the second surface power map.

It may be that the lens is a contact lens. In such embodiments, the portion of the lens may correspond to an optic zone of the contact lens. In such cases, it will be appreciated that references to an optic zone of a mould or an insert for a mould refer to the part of the mould which corresponds to the optic zone of a lens manufactured using that mould or insert.

Lenses, for example contact lenses, according to the present invention can be formed by cast moulding processes, spin cast moulding processes, or lathing processes, or a combination thereof. As understood by persons skilled in the art, cast moulding refers to the moulding of a contact lens by placing a lens forming material between a female mould member having a concave lens forming surface, and a male mould member having a convex lens forming surface.

In embodiments in which the ophthalmic lens comprises a contact lens, the contact lens material, as it is used as a part of a contact lens or as an entire contact lens, is visually transparent (although it can include a handling tint). The contact lens material can be a hydrogel material, a silicone hydrogel material, or a silicone elastomer material, as understood in the art. In other words, the present contact lenses can comprise, consist essentially of, or consist of a hydrogel material, a silicone hydrogel material, or a silicone elastomer material. As understood in the field of contact lenses, a hydrogel is a material that retains water in an equilibrium state and is free of a silicone-containing chemical. A silicone hydrogel is a hydrogel that includes a silicone-containing chemical. Hydrogel materials and silicone hydrogel materials, as used herein, have an equilibrium water content (EWC) of at least 10% to about 90% (wt/wt). The hydrogel material or silicone hydrogel material may have an EWC from about 30% to about 70% (wt/wt). In comparison, a silicone elastomer material, as used herein, has a water content from about 0% to less than 10% (wt/wt). Typically, the silicone elastomer materials used with the present methods or apparatus have a water content from 0.1% to 3% (wt/wt). Alternatively, examples of the present contact lenses can be made from rigid gas permeable materials, such as polymethyl methacrylate (PMMA) and the like.

The present methods may include a step of forming a contact lens in a moulding assembly, which comprises a first mould part and a second mould part assembled together. In the case of hydrogel lenses or silicone hydrogel lenses, the lenses can be made by polymerizing a hydrogel or silicone hydrogel lens formulation that includes a polymerization initiator in a lens shaped cavity formed between the first mould part and the second mould part. For silicone elastomer lenses, the lenses can be made by curing, vulcanizing, or catalysing, such as by hydrosylation, a liquid silicone elastomer material in a lens shaped cavity formed between the first mould part and the second mould part. The surface of each mould part that forms the contact lens shaped cavity may be convex, concave, planar or a combination of thereof. After formation of the contact lens, the two mould parts are separated such that the contact lens remains attached to the surface of one of the mould parts. As a result, a contact lens is provided on a surface of the first or second mould part. In some other embodiments, it may be desirable to place the lens on a surface of a mould part that was not used to produce the first lens member, but that may require additional steps to achieve the desired alignment of the member to the mould part. The lenses may then be removed from the mould part to which they are attached, and further processed, such as by extraction and hydration, and inspected, and packaged in a package and sterilized.

FIG. 1 shows a contact lens 10 according to embodiments of the invention. The contact lens 10 comprises an optic zone 11 and a peripheral zone 13. The optic zone 11 comprises the part of the lens through which a wearer of the contact lens sees. The optic zone 11 forms a lens designed to provide vision correction to the wearer. The peripheral zone 13 surrounds the optic zone 11 and does not provide any vision correction to the wearer. The peripheral zone 13 may perform other functions. For example, the peripheral zone 13 may serve to help maintain the contact lens on the wearer's eye. The peripheral zone 13 may include a ballast in order to maintain a predetermined orientation of the contact lens on the wearer's eye.

The two surfaces of the contact lens are shaped such that they vary across the optic zone 11 to form first and second surface power maps. The first and second surface power maps together form a lens power map. Thus, the optic zone can be said to provide a first surface power map, a second surface power map, and a lens power map. Within the optic zone the power maps may comprise one or more distinct regions. The example contact lens shown in FIG. 1 comprises a central region 15, an outer region 17, and a transition region 19. The outer region 17 surrounds the transition region 19. The transition region 19 surrounds the central region 15. The central region 15 and the outer region 17 may provide differing arrangements of lens power, such that they provide different vision corrections. The transition region 19 may serve for provide a smooth transition between the central region 15 and the outer region 17. It will be appreciated that the contact lens illustrated in FIG. 1 is provided merely as an example, and that other contact lenses according to the invention may include more or fewer regions. For example, some contact lenses according to embodiments of the invention may omit the transition region, or some contact lenses may even comprise only a single region across the whole of optic zone 11. Other contact lenses according to embodiments of the invention may include additional regions, for example formed as concentric circles.

According to a first example embodiment of the invention, there is provided a multifocal contact lens. It will be appreciated that alternative embodiments may comprise an intraocular lens or a spectacle lens. The multifocal contact lens comprises a first surface and a second surface. In this example embodiment, the first surface comprises an outer surface of the contact lens and the second surface comprises an inner surface of the contact lens. It will be appreciated by the person skilled in the art that the outer surface is the convex surface of the contact lens adjacent to a wearer's eyelid and that the inner surface is the concave surface of the contact lens adjacent the wearer's eye.

A portion of the first surface is shaped to form a first surface power map. A corresponding portion (for example, an opposing portion) of the lens is shaped to form a second surface power map. Thus, it can be said that a portion of the lens comprises first and second surfaces, forming respective first and second surface power maps. In this example embodiment, the portion corresponds to an optic zone of the contact lens. Thus, in this example embodiment, it can be said that a first surface of the optic zone forms the first surface power map and a second surface of the optic zone forms the second surface power map. It will be appreciated by the skilled person that the first surface power map shows the modification to the overall contact lens power map provided by the shape of that surface. Thus, a contact lens having two surfaces (an inner surface and an outer surface) comprises two surface power maps, the combination of which determines the overall contact lens power map.

Figure 2:
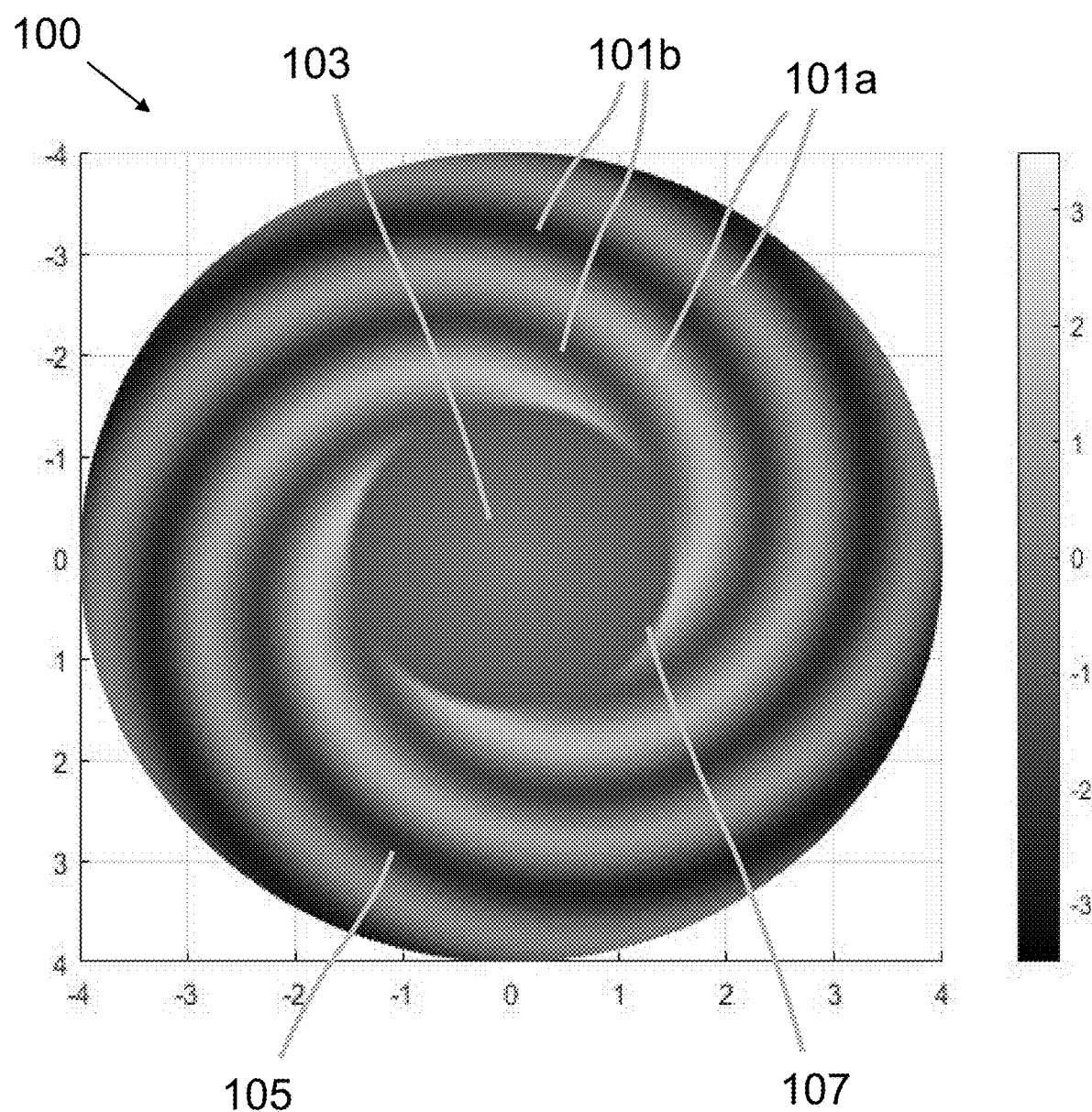
FIG. 2 shows a power map of a first surface of an optic zone of a contact lens according to a first embodiment of the invention.

FIG. 2 shows the first surface power map 100. The first surface power map 100 forms a spiral. The spiral varies across the portion, as is explained in further detail below. The spiral comprises a plurality of (in this example 4) arms 101. Each of the arms 101 comprises one of a peak arm 101a and a trough arm 101*b*. It will be appreciated that a peak arm 101*a* is an arm which constitutes a positive excursion of lens power, and that a trough arm 101*b* is an arm which constitutes a negative excursion of lens power.

The spiral can be considered to be formed by a summation of a plurality of components. In this case, the plurality of components includes a first periodic component in a radial direction extending outwards from the centre of the portion and a second periodic component in an azimuthal direction about the centre of the portion. In addition, the plurality of components further comprises an offset in power, the offset changing according to a radial distance from the centre of the portion. Thus, the spiral can be said to comprise a variation across the portion. In this example embodiment, the centre of the portion lies on the optical axis of the lens. It will be appreciated that an optical axis of a lens is equivalent to an optical axis of the optic zone of that lens.

In this example embodiment, the offset changes across the portion from +0 D at an inner part of portion to −3.0 D at the periphery of the portion. It will be appreciated that, in this example embodiment, which includes central and outer regions, the inner part of the lens corresponds to the innermost part of the outer region. In this example embodiment, the offset varies linearly. In other embodiments, the offset may vary in other ways, for example exponentially and/or monotonically. The periodic components vary between +0 D and +3.0 D. It will be appreciated that the power at a given point of the first surface power map is determined by the combination of the offset and the periodic components. Other embodiments of the invention may include components other than simply an offset and radial and azimuthal periodic components. It will be appreciated that, in such embodiments, the overall surface power map is formed by the combination of all of those components. Thus, in this example embodiment, the power of a point on the surface power map varies across the portion from −3.0 D up to +3.0 D. It will also be noted that, due to the offset in power, the variation of the power is dependent on the position on the portion. Specifically, the power varies between −3.0 D and +0 D at the periphery of the portion, and between +0 D and +3.0 D at the inner part of the portion. Thus, the multifocal contact lens of this example embodiment can be considered to have a base lens power, which varies across the portion from +0 D at the centre of the portion to −3.0 D at its periphery, and an add power of +3.0 D provided by the periodic components. Such a contact lens may be suitable for a patient who suffers from both myopia and presbyopia. The −3.0 D base lens power serves to correct the wearer's distance vision, whilst the +3.0 D add power serves to correct for the wearer's near vision when the wearer is not able to sufficiently accommodate. It will be appreciated by a person skilled in the art that the specific values of the first lens power and the second lens power (and therefore the base lens power and add power) provided are purely examples, and that the actual values used in a given situation will be determined by the needs of the intended wearer.

In this example embodiment, the period of the radial variation is 1.2 mm and the period of the azimuthal variation is 90 degrees. However, it will be appreciated that, in alternative embodiments, other periods of the radial and/or azimuthal variation may be used.

In this particular embodiment, the power varies smoothly across the first surface power map 100, substantially as a sinusoid in both the radial and azimuthal directions. Having the surface power map vary smoothly across the portion of the lens provides for easier manufacture using a lathe of the contact lens or of apparatus (for example, a mould or an insert for a mould) for manufacturing the contact lens. However, in alternative embodiments, the power may vary according to other waveforms. For example, the power may vary as a square wave or as a rounded square wave in one or both of the radial and azimuthal directions. Thus, in alternative embodiments, the power need not necessarily vary smoothly across the portion of the lens.

In this example embodiment, the positive and negative excursions of the periodic components are of equal length, such that they can be said to have a 50% duty cycle. Alternative embodiments comprise periodic components having other duty cycles. Thus, in such embodiments, the positive excursion may be of a different length than the negative excursion. Such embodiments can bias the periodic components towards a particular lens power, for example by providing a greater quantity of a first lens power than a second.

It will be appreciated that the width of the arms 101 of the spiral is determined at least in part by the ratio of the period of the radial variation to that of the azimuthal variation. In this example embodiment, each arm 101 of the spiral is approximately 500 microns wide. It will be appreciated that alternative embodiments may incorporate arms 101 having different widths. It will also be appreciated that the width of an arm 101 is defined as its perpendicular width. In this embodiment, all of the arms of the spiral are of equal width however, in other embodiments, one or more arms of the spiral may be of a different width to the other arms of the spiral.

Similarly, in this example embodiment, the periods of the first and second periodic components are each substantially constant across the portion. However, in alternative embodiments, the period of at least one of the first and second periodic components may change according to one or both of a radial distance from the centre of the portion and an azimuthal position about the centre of the portion.

In alternative embodiments, the period of the second periodic component is less than 180°. It will be appreciated by a person skilled in the art that the period of the second periodic component determines the number of arms 101 on the spiral. Thus, in such embodiments, the spiral comprises at least two arms. It will therefore also be appreciated that certain values of the period of the second periodic component, specifically those which are unit fractions of 360 degrees, may be particularly advantageous in that they allow for a surface power map without azimuthal discontinuities.

In this example embodiment, each arm 101 of the spiral twists through an angle of 270 degrees (or 0.75 of a rotation). In alternative embodiments of the invention, each arm 101 of the spiral may twist through between a quarter of a rotation (90 degrees) and 40 rotations. In this example embodiment, the arms of the spiral twist at a constant rate across the portion. Thus, the arms can be said to have a constant twist rate. In other embodiments, the twist rate of the arms may vary across the portion.

In this particular embodiment, the first surface power map 100 comprises a central region 103 and an outer region 105. The central region 103 immediately surrounds the optical axis of the contact lens. The outer region 105 surrounds the central region 103. The power of the central region does not vary periodically across the central region 103 and may, for example, be substantially constant across the central region 103. The outer region 105 comprises the spiral power map. In alternative embodiments of the invention, each arm 101 of the spiral extends from the centre of the portion of the lens to the periphery of the portion. Thus, such embodiments do not comprise distinct central and outer regions.

As has been previously mentioned, in this example embodiment, the portion of the lens corresponds to the optic zone of a contact lens. In this example embodiment, the central region 103 has a diameter of 2 mm, which corresponds to 25% of the 8 mm diameter of the optic zone. The optic zone, through which the wearer sees, provides the first surface power map shown in FIG. 1. The contact lens may in addition comprise a surrounding peripheral zone, which provides no additional focussing or vision correction and serves merely to help maintain the contact lens in position on the wearer's eye. The diameter of the central region may be less than 25% of that of the optic zone. However, it will be appreciated that, in alternative embodiments of the invention, the diameter of the central region 103 may take other values. Similarly, it will be appreciated that the ratio of the diameter of the central region 103 to that of the optic zone may also take other values. For example, the diameter of the central region 103 may be less than 30% of that of the optic zone.

The central region 103 may be smaller than the minimum pupil size of a wearer of the contact lens. Such embodiments maintain multifocal vision even when the wearer's pupil constricts to its minimum size. If the central region 103 is larger than the minimum pupil size, when the wearer's pupil constricts to its minimum size, only the central region 103 will be positioned across the wearer's entrance pupil. As the power of the central region 103 does not vary as a spiral across the central region 103, the lens will not provide multifocal vision for any pupil sizes smaller than the central region 103.

Advantageously, in this example embodiment, the central region 103 provides a lens power corresponding to distance vision. Generally, brighter conditions correspond to outdoors environments. Thus, the wearer's pupil is typically more constricted when outdoors than when indoors. In addition, the wearer generally has greater need for distance vision when outdoors than when indoors. Having a central region 103 with a lens power corresponding to distance vision can allow the contact lens to provide high acuity distance vision even when the wearer's pupil is constricted to its minimum size.

This example embodiment further comprises a transition region 107. The transition region 107 surrounds the central region 103. The outer region 105 surrounds the transition region 107. The power of the transition region 107 varies to provide a smooth transition between the central region 103 and the outer region 105. It will be appreciated that such a transition region 107 is not essential and therefore that alternative embodiments do not include a transition region 107. It will be appreciated that smooth, in this context, is defined as being smooth enough for the corresponding lens curvature to be reproduced by a lathe. In this example embodiment, the transition region is approximately 300 microns wide. It will, however, be appreciated that other widths of transition region may also be used.

It will be appreciated by the skilled person that the second surface of the portion of the contact lens (i.e. the second surface of the optic zone of the contact lens of this example embodiment) forms a second surface power map. In this example embodiment the second surface power map does not vary periodically across the portion, providing a substantially constant +0 D power across the portion. Therefore, the contact lens has a lens power map which matches the first surface power map. The contact lens therefore provides reduced variation in the ratio of near focussing to distance focussing as the wearer's pupil changes size.

Whilst in this example embodiment the first surface corresponds to the outer surface of the contact lens and the second surface corresponds to the inner surface of the contact lens, a person skilled in the art will appreciate that, in alternative embodiments, the first surface may correspond to the inner surface and the second surface may correspond to the outer surface. Thus, in embodiments, the inner surface comprises a surface power map forming a spiral and the outer surface comprises a surface power map having substantially constant power across the surface power map.

Figure 3:
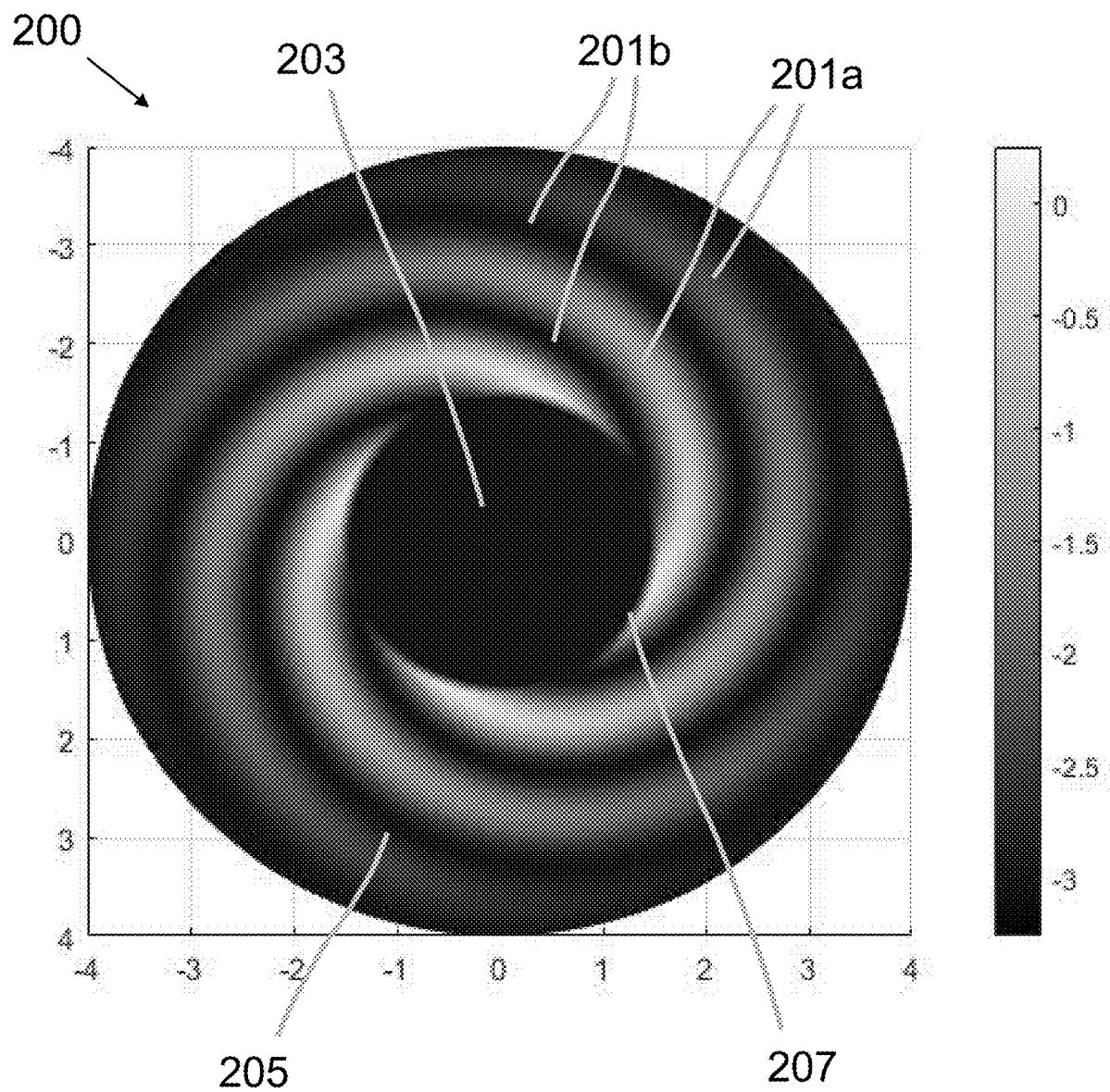
FIG. 3 shows a lens power map of a first surface of an optic zone of a contact lens according to a second embodiment of the invention.

FIG. 3 shows a second multifocal contact lens according to a second example embodiment of the invention. The contact lens comprises a first surface power map 200 substantially as described in respect of the first embodiment, but for the following features. The first surface power map 200 of the second embodiment does not comprise an offset in power. Thus, the first surface power map can be said to comprise a base lens power which is substantially constant across the portion. Furthermore, the magnitude of the spiral varies across the portion with respect to a radial distance from the centre of the portion. That is to say that a magnitude of each of the periodic components varies according to a radial distance from the centre of the portion. In this example embodiment, the magnitude of the periodic components is at its maximum at the innermost part of the outer region and decays linearly with radial distance from the centre of the portion. Thus, the spiral once again comprises a variation across the portion. The second surface power map 200 is the same as that of the first embodiment. Thus, the lens power map matches that the first surface power map 200.

A third example embodiment of the invention provides a third multifocal contact lens. The third multifocal contact lens is substantially as described in respect of the first embodiment except of the following features. In this case, the offset in power is not provided by the first surface power map, but the offset in power is instead provided by the second surface power map. Thus, the first surface power map can be said to comprise a spiral which does not comprise a variation across the portion. However, the lens power map (being formed by the combination of the first and second surface power maps) still comprises a spiral having a variation across the portion, the variation being imparted by the offset in power provided by the second surface power map. Thus, the contact lens of this embodiment provides a lens power map which matches that of the first embodiment.

According to a fourth example embodiment of the invention, there is provided a fourth multifocal contact lens. A first surface power map of the fourth contact lens is identical to that of the contact lens of the second embodiment. In this embodiment, the second surface power map also comprises a spiral formed by a summation of a plurality of components. The plurality of components comprises a first periodic component in a radial direction extending outwards from the centre of the portion and a second periodic component in an azimuthal direction about the centre of the portion. As in the case of the first surface, the spiral comprises a plurality of arms, including peak arms and trough arms. In this example embodiment, the periodic components of the second surface power map are the same as those of the first surface power map. However, a skilled person will appreciate that alternative embodiments may incorporate periodic components having different periods on the second surface power map to one or both of those of the first surface power map. In this example embodiment, the second surface power map also comprises a central region, an outer region, and a transition region.

In this example embodiment, the spiral formed by the second surface power map twists in the opposite direction to that formed by the first surface power map. Thus, in this particular embodiment, the spirals provided by the first surface power map and the second surface power map have opposing twist directions. In this example embodiment, the spiral formed on the first and second power maps are substantially identical apart from the opposing twist directions. The power map of the contact lens is determined by the superposition of the first surface power map and the second surface power map.

Figure 4:
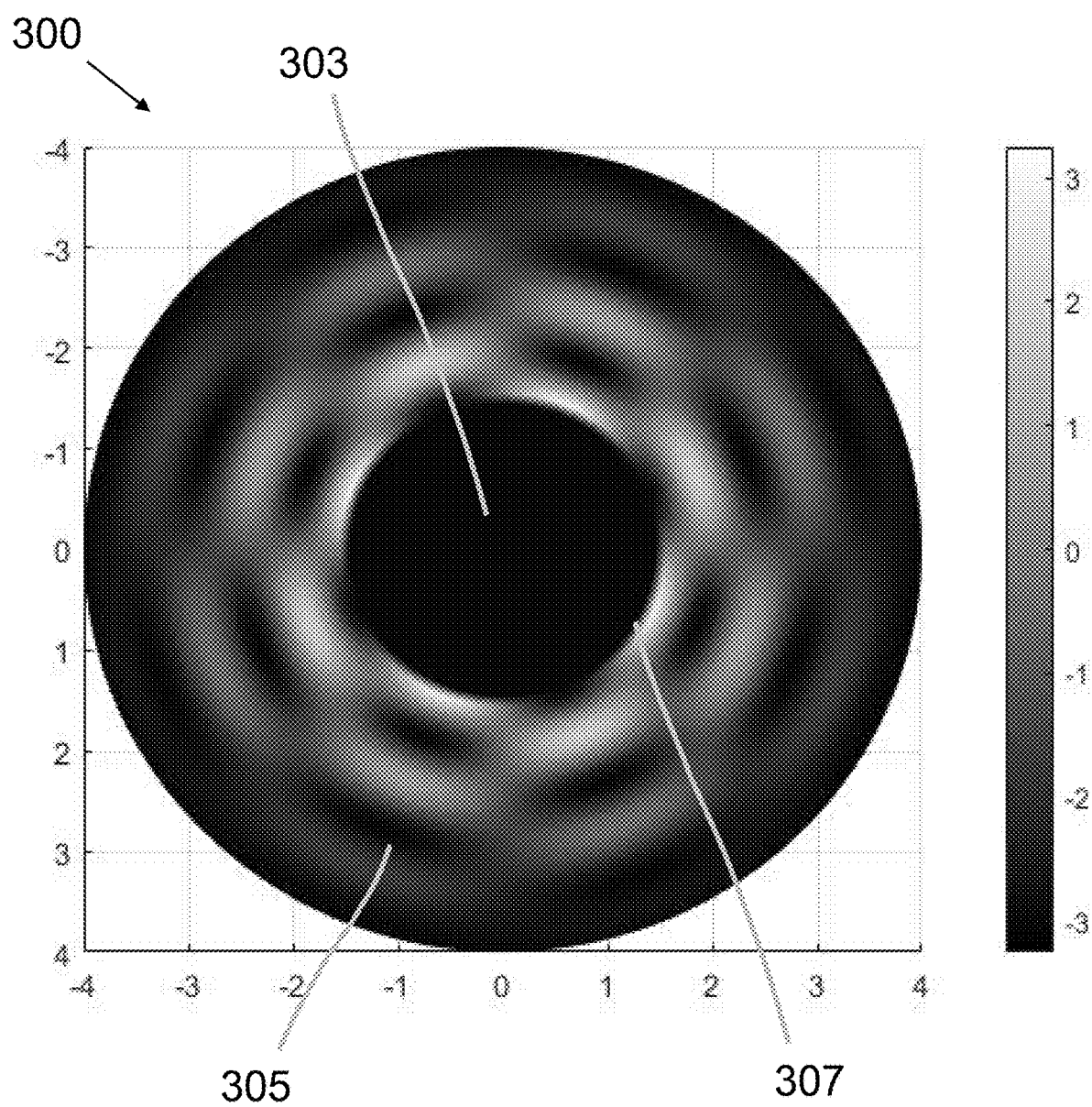
FIG. 4 shows a lens power map of the optic zone of a contact lens according to a third embodiment of the invention.

FIG. 4 shows a lens power map 300 of the contact lens. The superposition of the two counter-rotating spirals formed by the first surface power map and the second surface power map results in a lens power map 300 which approximates a pseudo-dartboard pattern of alternating annular rings. The contact lens also provides a monotonic change in the ratio of the first lens power to the second lens power as a wearer's pupil constricts. Thus, the contact lens also provides improved multifocal vision in the presence of variable light conditions. As both the first surface power map and the second surface power map comprise central, outer, and transition regions, the overall lens power map 300 of the contact lens also comprises a central region 303, an outer region 305, and a transition region 307.

According to a fifth embodiment of the invention, there is provided a spectacle lens. The spectacle lens comprises a lens power map substantially as described in respect of the first embodiment of the invention. It will, however, be appreciated by the skilled person that a spectacle lens does not comprise an optic zone in the same sense as the contact lenses of the first embodiment. In the case of spectacle lenses, typically substantially all of the lens can be considered to be an optic zone of the lens The skilled person will further appreciate that characteristics of the lens profile defined above in relation to the optic zone of a contact lens are similarly applicable in relation to the portion of the spectacle lens of the present embodiment. It will be appreciated that alternative embodiments of the invention comprise spectacle lenses having surface power maps substantially as described in respect of the second, third, and fourth embodiments of the invention. Spectacle lens 700 comprises a central region 715, an outer region 717, and a transition region 719. In this example embodiment, the spiral(s) formed by one or both of the first and second surface power maps do not extend to the left-most edge of the spectacle lens 717. Instead, the spirals only extend out to dashed line 701. It may be that the spirals decay in magnitude (for example, linearly) from the boundary between the transition region 719 and the outer region 717 as they extend outwards to dashed line 701. In other embodiments, the spirals may have substantially constant magnitude across the outer zone 717. In such embodiments, the spectacle lens 700 may further comprise a narrow blending region running along dashed line 701. It will further be appreciated that, in other embodiments, the spirals continue outwards to the edges the spectacle lens 700. In this example embodiment, the central region 715 (and the surrounding transition region 719 and outer region 717) is not positioned in the geometric centre of the spectacle lens 700, and can be said to be offset from the geometric centre of the spectacle lens 700. It will be appreciated by the skilled person that such an offset may serve to place the central region in the part of the spectacle lens 700 through which a wearer most frequently looks.

According to a sixth embodiment of the invention, there is provided an intraocular lens. The intraocular lens comprises a spiral power substantially as described in respect of the first embodiment of the invention. It will be appreciated that alternative embodiments of the invention comprise intraocular lenses having surface power maps substantially as described in respect of the second, third, and fourth embodiments of the invention.

Figure 5:
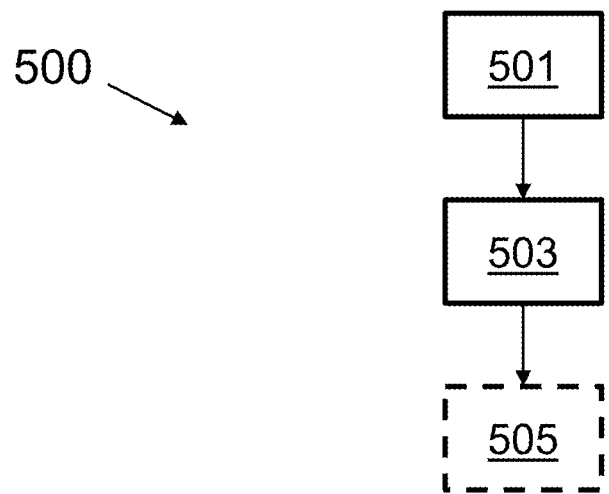
FIG. 5 shows a flow chart illustrating the steps of a method according to a fourth embodiment of the invention.
Figure 6:
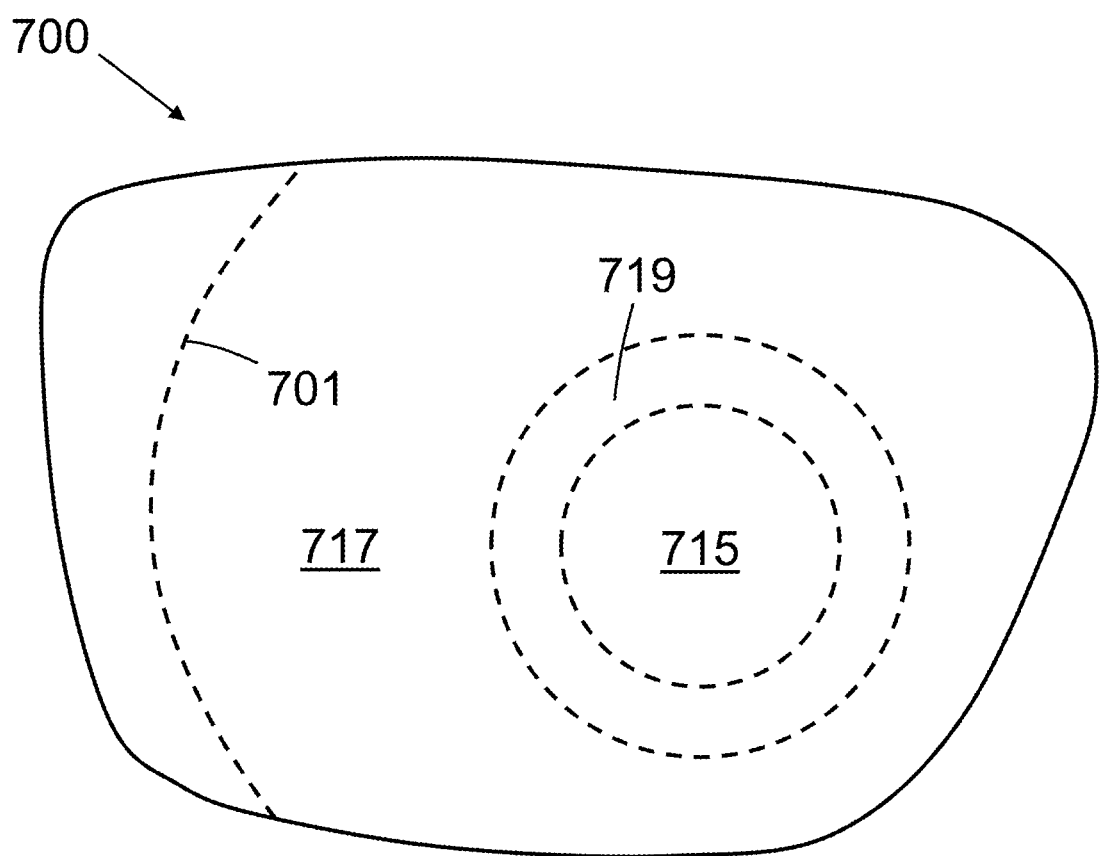
FIG. 6 shows a spectacle lens according to example embodiments of the invention.

FIG. 5 shows a flow chart illustrating the steps of a method 500 of manufacturing a lens, for example a contact lens, according to a seventh embodiment of the invention.

A first step of the method 500, represented by element 501, comprises operating a lathe to shape a first surface of a portion of one of: a lens, a mould for a lens, or an insert for manufacturing a mould for a lens. The first surface is shaped such that the first surface varies across the portion of the lens (which may, for example, be an optic zone of a contact lens) to form a first surface power map.

A second step of the method 500, represented by element 503, comprises operating a lathe to shape a second surface of the portion. That is to say, the second step comprises operating a lathe to shape a second surface of a corresponding (for example, opposing) portion of one of the lens, a mould for the lens, or an insert for manufacturing a mould for the lens. The second surface is shaped such that the second surface varies across at least the portion of the lens to form a second surface power map.

The first surface power map and the second surface power map together form a lens power map. The first surface power map, the second surface power map, or the lens power map comprises a spiral. The spiral varies across the portion.

It may be that the first surface power map comprises the spiral. Alternatively, or additionally, it may be that the second surface power map comprises the spiral. It may be that the lens power map comprises the spiral (i.e. the spiral is formed by the combination of the first and second surface power maps). The second surface may be shaped to vary as a mirror image of the first surface. Alternatively, the second surface may be shaped such that a spiral formed on the first surface power map twists in the opposite direction to a spiral formed on the second surface power map.

When the first surface (and the second surface where the second step 503 has been performed) are comprised on a mould for a lens or an insert for a mould for a lens, the method 500 may comprise an optional third step, represented by element 505. The third step 505 comprises using the mould of the insert for a mould for a lens to manufacture a lens.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

In the first embodiment a lens having a spiral lens power map was provided by a first surface power map of the contact lens comprising a spiral and a second surface power map of the contact lens having substantially constant power across the surface power map. However, in alternative embodiments, a lens having a spiral lens power map is provided by each of the first surface power map and the second surface power map comprising a spiral. In such an embodiment, the periods and phases of the periodic components of the second surface power map are the same as those of the first surface power map. Thus, the first and second surface power maps can be said to comprise mirror images of one another. The first and second surface power maps therefore superpose to form a single spiral power map and thereby a contact lens having a spiral lens power map.

In all of the first, second, third, and fourth embodiments, the lens power maps of the contact lens each comprise a central region having substantially constant power profile, an outer region incorporating the spiral power profile, and a transition region providing a smooth transition between the central and outer regions. However, some alternative embodiments do not incorporate a transition region. Further alternative embodiments do not incorporate distinct central and outer regions. Instead, in such embodiments, the spiral profile extends from the centre of the portion of the lens all of the way out to the radial periphery of the portion.

In the first embodiment, the spiral formed by the first surface power map twists in an anticlockwise direction. However, in alternative embodiments, the spiral formed by the first surface power map twists in a clockwise direction. In those embodiments where mirrored spirals are formed on the first and second surface power maps, the spirals may rotate in either a clockwise or an anticlockwise direction. Similarly, in the fourth embodiment, the spiral formed on the first surface power map twists in an anticlockwise direction and the spiral formed on the second surface power map twists in a clockwise direction. However, in alternative embodiments, the spiral formed on the first surface power map twists in a clockwise direction and the spiral formed on the second surface power map twists in an anti-clockwise direction.

In some embodiments of the invention, the spiral formed on one or both of the first and second surface power maps changes its direction of rotation at a pre-determined radial distance from the centre of the portion. For example, the spiral may rotate in a clockwise direction between the centre of the portion and the pre-determined radial distance, and in an anti-clockwise direction beyond the pre-determined radial distance. In some embodiments, the lens incorporates more than one change in the direction of rotation of the spiral. Thus, the spiral may, for example, change from a clockwise rotation to an anti-clockwise rotation before reverting to a clockwise rotation again. It will be appreciated by the skilled person that the lens can incorporate any number of changes in the direction of rotation of the spiral. It will also be appreciated that each of those changes in direction can take place at any chosen radial distance from the centre of the portion. The power map may therefore comprise annular rings alternating between clockwise and anti-clockwise rotating spirals.

In some embodiments, between regions of the ophthalmic lens having different directions of rotation, there is a region in which the power map does not vary as a spiral. For example, the region may have a substantially constant power. For example, from the centre of the portion to a first radial distance, the lens (or surface) power map may vary as a clockwise rotating spiral, followed by a region of substantially constant power, before varying as an anti-clockwise rotating spiral. The power map may therefore appear to comprise a plurality of annular rings, for example alternating between a spiral and substantially constant power, wherein the spiral regions also alternate between clockwise and anti-clockwise rotation.

Similarly, in some embodiments, the spiral may be interrupted by one or more regions, for example rings, in which the power map does not vary as a spiral. For example, the region may have a substantially constant power. Thus, for example, the power map may comprise annular rings alternating between a spiral and substantially constant power. In such embodiments, the spiral may change its direction of rotation between each interruption, or it may continue with its previous direction of rotation. Thus, the spiral may maintain a constant direction of rotation across the lens, but the spiral may be interrupted by regions of substantially constant lens power.

Whilst embodiments of the invention have been described above in relation to a method of manufacturing contact lenses, moulds for contact lenses, or inserts for moulds for contact lenses using a lathe, it will be appreciated that other methods of manufacture are also possible. In particular, the moulds or the inserts may also be manufactured using additive manufacturing techniques, for example by 3D printing.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A multifocal ophthalmic lens, wherein:
   a first surface of the lens is shaped to form a first surface power map;
   a second surface of the lens is shaped to form a second surface power map;
   the first and second surface power maps together form a lens power map;
   the first surface power map, the second surface power map, or the lens power map comprises a spiral, the spiral having a variation across at least a portion of the lens, the spiral having a first periodic component, in a radial direction extending outwards from the centre of the portion, and a second periodic component having a substantially constant period, in an azimuthal direction about the centre of the portion.

2. The multifocal ophthalmic lens according to claim 1, wherein:
   the first periodic component has a period of greater than 100 microns; and
   the second periodic component has a period of greater than 6 degrees.

3. The multifocal ophthalmic lens according to claim 1, wherein the variation of the spiral comprises an offset in power, the offset changing according to a radial distance from the centre of the portion.

4. The multifocal ophthalmic lens according to claim 1, wherein a peak power of one or more arms of the spiral varies according to one or both of: a radial distance from the centre of the portion and an azimuthal position about the centre of the portion.

5. The multifocal ophthalmic lens according to claim 1, wherein:
   a peak power of each arm of the spiral does not vary with radial distance from the centre of the portion; and
   the peak power of at least one arm of the spiral differs from that of the other arms.

6. The multifocal ophthalmic lens according to claim 1, wherein each of the first surface power map and the second surface power map vary smoothly across the portion.

7. The multifocal ophthalmic lens according to claim 1, wherein:

the portion of the lens comprises a central region and an outer region, the outer region surrounding the central region;

the lens power map within the outer region comprises the spiral; and the lens power map does not vary periodically within the central region.

8. The multifocal ophthalmic lens according to claim 7, wherein the central region has a diameter of less than 50% of that of the portion.

9. The multifocal ophthalmic lens according to claim 7, wherein:

the lens comprises a transition region, the transition region surrounding the central region and the outer region surrounding the transition region; and the lens power map varies such that the transition region provides a smooth transition between the central zone and the outer zone.

10. The multifocal ophthalmic lens according to claim 1, wherein a twist rate of the spiral varies according to a radial distance from the centre of the portion.

11. The multifocal ophthalmic lens according to claim 1, wherein a width of one or more arms of the spiral differs from a corresponding width of the other arms of the spiral.

12. The multifocal ophthalmic lens according to claim 11, wherein, at a pre-determined radial distance from the centre of the portion, the spiral changes its direction of rotation.

13. The multifocal ophthalmic lens according to claim 1, wherein the ophthalmic lens is a contact lens, a spectacle lens, or an intraocular lens.

14. A method of manufacturing a multifocal ophthalmic lens, the method comprising:

operating a lathe to shape a first surface of one of: a lens, a mould for a lens, or an insert for manufacturing a mould for a lens to form a first surface power map;

operating a lathe to shape a second surface of the lens, mould, or insert to form a second surface power map;

wherein:

the combination of the first and second surface power maps forms a lens power map;

the first surface power map, the second surface power map, or the lens power map comprises a spiral, the spiral having a variation across at least a portion of the lens, mould or insert, the spiral having a first periodic component, in a radial direction extending outwards from the centre of the portion, and a second periodic component having a substantially constant period, in an azimuthal direction about the centre of the portion.

15. A method of improving vision of a person, the method comprising:

providing the multifocal ophthalmic lens according to claim 1 to a person in need of improved vision.

16. The multifocal ophthalmic lens according to claim 1, wherein the ophthalmic lens is a centre distance contact lens, or a centre near contact lens.

17. The multifocal ophthalmic lens according to claim 7, wherein the central region has an optical power corresponding to a distance vision correction.

18. The multifocal ophthalmic lens according to claim 7, wherein the central region has an optical power corresponding to a near vision correction.

* * * * *